United States Patent [19]

Calenoff et al.

[11] Patent Number: 4,963,356

[45] Date of Patent: Oct. 16, 1990

[54] STABLE ANTIGENIC EXTRACTS METHODS

[75] Inventors: Emanuel Calenoff, Burlingame; Myron A. Beigler, Los Altos Hills; Gerald L. Friesen, Vacaville; James L. Nichols, Los Altos, all of Calif.

[73] Assignee: Minnesota Mining and Manufacturing Company, St. Paul, Minn.

[21] Appl. No.: 40,216

[22] Filed: Apr. 20, 1987

Related U.S. Application Data

[63] Continuation of Ser. No. 433,962, Oct. 13, 1982, abandoned.

[51] Int. Cl.$^5$ .................. A61K 39/05; A61K 39/36; A61K 39/02
[52] U.S. Cl. ........................................ 424/91; 424/88; 424/92; 424/95; 514/2; 514/8; 530/322; 530/370; 530/395; 530/413; 530/414
[58] Field of Search ................. 424/88, 91, 92, 93; 514/2, 8; 530/322, 370, 395, 414, 413

[56] References Cited

U.S. PATENT DOCUMENTS

| | | | |
|---|---|---|---|
| 2,908,614 | 10/1959 | Muggleton | 435/188 |
| 4,350,686 | 9/1982 | Relyveld et al. | 424/88 |
| 4,387,091 | 6/1983 | Vijay et al. | 424/88 |

OTHER PUBLICATIONS

Mosbach, *Methods Enzymol*, vol. XLIV, 1976, pp. 784-790.

Bor, C. *Chem. Abst.*, vol. 96(16) No. 129761k, "Gamma Radiation Sterilization of Pharmaceutical Active Ingredients, Adjuvants and Packaging Materials".

*Primary Examiner*—Robin L. Teskin
*Attorney, Agent, or Firm*—Donald M. Sell; Walter N. Kirn; Philip M. Goldman

[57] ABSTRACT

A storage-stable, high potency allergenic extract is prepared by ultrafiltration, retaining fractions having molecular weights of from 1000 to 100,000, and drying the retained fraction to a moisture content of less than one weight percent. The extract can also be pretreated with amylase before ultrafiltration, treated with affinity chromatography before drying, and/or treated with gamma radiation after drying.

25 Claims, No Drawings

STABLE ANTIGENIC EXTRACTS METHODS

This is a continuation of application Ser. No. 433,962 filed Oct. 13, 1982 now abandoned.

FIELD OF THE INVENTION

This invention relates to allergenic materials used to diagnose and treat allergic conditions in humans. More specifically, this invention relates to improved extracts from plant and animal sources prepared by improved methods which concentrate the allergenically active components in a form suitable for use in diagnosis and treatment of allergic conditions. The extracts have greatly increased storage stability prior to and during use.

BACKGROUND OF THE INVENTION

Description of the Prior Art

A wide variety of allergenic extracts and methods for preparing, storing, and using them including standard commercial procedures are described in *Remington's Pharmaceutical Sciences*, p. 1344–1352, Mack, Easton, Pennsylvania, 15 ed. (1975). Allergenic extracts from a wide range of natural and plant and animal sources and manufactured goods are described. Manufacturing procedures for preparing extracts including details about grinding, defatting, extraction, clarification, dialysis, concentration, sterilization and lyophilization are presented therein.

Major efforts to concentrate and standardize allergenic components of allergen extracts have been made in the past. Procedures for solvent extraction, often combined with precipitation, are described in U.S. Pat. Nos. 2,316,311, 3,148,122, 3,281,323, 3,591,677, 3,953,588, 3,995,023, 4,027,006, and 2,347,435. Ion exchange techniques are described in 2,901,398. The principal objective of these processes is to separate the active allergenic components from inactive ingredients obtained through the particular extraction procedure employed.

A number of patents have been directed to the preparation of modified allergenic compounds wherein the allergenic component is chemically modified such as by cross-linking with formaldehyde or other reactive chemical agent. As a preliminary procedure, the allergenic extracts may be separated from low molecular weight components which would interfere with the chemical reaction. Removal of lower molecular weight components for this purpose is described in U.S. Pat. No. 4,226,853 by (dialysis), 4,234,569 (ultrafiltration or gel filtration), 4,256,732 (dialysis), and 4,163,778 (dialysis and column chromatography). In the above procedures, the aqueous or ethanolic extract solution is treated to remove the lower molecular weight components, and the chemical reactants are added to the aqueous solution of the product to effect the chemical modification of the allergenic protein.

Of a similar nature are the papers by E. Puttonen et al, "Studies on Allergen and Allergoid Preparations for Purified Timothy (Phleum pratense) Pollen Extracts" in *Int. Arch. Allergy Appl. Immun.* 68:1–12 (1982). In this paper, fractionation of a dried timothy pollen extract by gel column chromatography is presented. In the procedure, a sample of the extract was fractionated with a SEPHADEX G-75 column, and active fractions were pooled and freeze-dried. One portion of the material was then reacted with formaldehyde to prepare an allergoid product, and the properties of the original and treated fractions are compared.

The freeze-dried timothy grass pollen intermediates described in the Puttonen et al article are completely different from the extracts of this invention. In the sampling of active fractions for pooling, minor allergens are discarded, and the relative ratios of allergens present in the original extract are not preserved. The freeze-dried product cannot therefore be correlated with diagnostic or desensitizing compositions which are based on the natural allergen composition profile. This publication does not describe separation of plant extracts using ultrafiltration or lowering the moisture content of the resultant solution to less than one weight percent to increase the shelf life stability thereof.

Stability studies of timothy grass pollen extracts are disclosed by M.C. Anderson et al in "Antigenic and Allergenic Change During Storage of a Pollen Extract", *J. Allergy Clin. Immunol.* 69(1) pp 3–10 (1982) and articles cited therein. Enzyme activities of timothy pollen extracts are reported, and degradation mechanisms including thermal denaturation and enzymatic breakdown of allergenic and antigenic proteins and carbohydrates is postulated. Sugar-splitting activity was reported to be inhibited in 50 percent glycerol solutions.

SUMMARY AND OBJECTS OF THE INVENTION

The process of this invention for increasing shelf life stability of allergenic extracts comprises passing a solution of the allergenic extract through 100,000 dalton and 1000 dalton filters and retaining the fraction having a molecular weight of from 1000 to 100,000, and drying the retrained fraction to a moisture content of less than one weight percent without denaturing the allergens. The product has improved stability, as measured by the STORAGE STABILITY TEST described hereinafter, both as a moisture-free powder and as a reconstituted aqueous solution. This process can be used to treat allergenic extracts selected from the group of plant and animal extracts including pollens, molds, smuts and animal products such as epidermals, glandular elements, insects and insect venoms, and foods, for example.

The stabilized allergenic extracts of this invention comprise extracted allergens having molecular weights within the range of from 1000 to 100,000 and a moisture content of less than one weight percent. These extracts are substantially free from extracted components having molecular weights of less than 1000 and greater than 100,000. Preferably, the allergenic extracts are substantially free from active proteolytic agents and starch reducing agents.

One embodiment of the product of this invention comprises insoluble supports upon which the allergenic extracts of this invention are supported, for example by absorption, adsorption or chemical bonding, to yield diagnostic means with greater chemical specificity.

It is an object of this invention to provide stable, sterile, virus-free allergenic products derived from extracts obtained from plant and animal sources.

It is a further object of this invention to provide a more efficient process for making and stabilizing sterile, viral-free allergenic extracts obtained from plants and animal sources.

It is a further object of this invention to provide stabilized allergenic products which have greater chemical specificity when used as diagnostic reagents than extracts which have not undergone this treatment.

It is a still further object of this invention to provide diagnostic supports having, thereon, the superior, stabilized, highly specific allergenic products of this invention.

DETAILED DESCRIPTION OF THE INVENTION

Desensitizing treatments with allergenic extracts corresponding to the allergen causing an allergic reaction are often used by medical specialists to treat severe allergic conditions. Allergic reactions most generally treated derive from pollens originating from trees, grasses, weeds and garden plants; epidermals and miscellaneous inhalents such as dust, tobacco, and glandular elements; molds; smuts; insects and insect venoms; and foods including animal and vegetable proteins, seafoods, eggs, milk and the like. The generally accepted medical procedure for treating severe allergic conditions involves the testing and administration of crude extracts obtained from the suspected cause of the original allergic condition. In general, the extracts are purified to remove some non-antigenic material by general procedures including some or all of the following technioues: grinding, defatting, extracting, clarifying, dialyzing, concentrating and sterilization. These procedures are relatively simple and yield antigenic materials mixed with other components derived from either the plant or animal source or the extraction procedures. Previously proposed separations by precipitation, chromatography, ultrafiltration, and solvent extraction have not been adopted because they were not found to improve the product.

A major limitation of the currently available full strength antigenic compositions is their lack of shelf life stability. Efforts to increase stability by chemical treatment have generally reduced the antigenicity.

The method of this invention is a process which can be easily followed using currently available technology to yield an antigenic product having no significant reduction in antigenicity. The products contain all of the representative antigenic materials derived from the original plant or animal source. The purified product of this invention is more stable than previously known formulations, can be more easily standardized and is the ideal allergenic product to be used for diagnostic purposes and for desensitization treatments.

This process, starting with the allergenic extract, comprises the separation of the allergenic extract by ultrafiltration using 1000 and 100,000 dalton filters. All components having a molecular weight of less than 1000 daltons and greater than 100,000 daltons are then discarded. The retained fraction has a molecular weight of from 1000 to 100,000 and is essentially free from components having higher and lower molecular weights. This retained fraction is dried to a moisture content of less than one weight percent to yield an antigenic product.

The ultrafiltration process of this invention produces a sterile product with all of the original allergens in the ratios present in the original complete extract. This product has substantially greater shelf life stability than a dried product of the previously known extracts as measured in STORAGE STABILITY TEST. The mechanisms of degradation processes are not clearly understood. Studies made with only a few allergens have been reported, and there is no established common cause of instability even between the few studied. Without being limited to any theory, we believe that a significant cause if not the major cause of instability is due to Maillard reactions between sugars and the proteins. Not only would this introduce toxic reaction products in the extracts but it would directly degrade the protein and glycoprotein allergens.

The ultrafiltration with a 1000 dalton filter removes sugars, amino acids and peptides which would undergo Maillard reaction changes. The ultrafiltration with a 100,000 dalton ultrafilter efficiently removes proteolytic and starch reducing enzymes having a molecular weight above 100,000 along with bacteria, virus and non-allergenic impurities, and without disturbing the allergen content of the extract. The level of proteolytic or carbohydrate reducing enzymes would be reduced. Accordingly, the level of proteolytic activity would be lowered. Perhaps more importantly, the carbohydrate reducing activity which would convert starches to reducing sugars would be diminished. Consequent Maillard reactions would be greatly reduced because of the low levels of sugar formed. Consequently original allergen levels would be preserved, and formation of pigments and toxic by-products would be minimized.

In one embodiment of this invention, the extracts are treated to convert polysaccharides and starches to sugars by passing them through an amylase column before the ultrafiltration steps. Suitable amylase columns contain solid supports to which amylase has been attached by covalent bonding. Suitable bonding procedures are described by Ichiro Chibata in *Immobilized Enzymes*, Halsted Press, New York (1978), and by A. Cuatrecasas, *J. Bio. Chem* 245 3059 (1970), the entire contents of which are hereby incorporated by reference. No polysaccharides, starches or sugars remain in the final product after ultrafiltration in the procedure.

In a still further embodiment of the invention, the extract is passed through an affinity column containing, on an insoluble support, compounds which selectively bind to enzymes remaining in the extract following the ultrafiltration such as any remaining proteolytic agents and carbohydrate reducing agents. The antibodies which selectively bind to those enzymes are commercially available or they can be readily prepared by conventional procedures from the enzymes. Examples of enzymes which would remain after the ultrafiltration (if present in the extract) are alpha-trypsin, chymotrypsin, and some acid phosphatases, for example. The anti-trypsin, anti-chymotrypsin factors and antibodies to other enzymes are bound to insoluble supports, and the extracts are passed through columns containing the bound anti-enzyme. The enzymes by conjugating to their anti-enzyme are removed from the extract. Techniques for binding the enzymes are described in *Immobilized Enzymes*, supra.

Greatly extended storage under moisture-free conditions (less than one percent moisture) and as reconstituted aqueous solutions is achieved with this process. Sterilization without the use of potentially degrading severe sterilizing thermal, radiation or chemical treatments is also achieved.

The ultrafiltration procedures used are conventional and known in the art. The allergenic extracts are passed through the ultrafilters as aqueous solutions, preferably buffered to a pH of from 6 to 8. Suitable buffer solutions include standard solutions such as Phosphate Buffer Solution (PBS), Coca's Solution and the like. Salt solutions such as sodium chloride solutions can also be employed. The dissolved solids concentration is not critical, concentrations of less than 20 weight percent solids being generally operable. Preferred concentrations are less than 5 weight percent dissolved solids, and concentrations of less than 2 weight percent are optimum. Ultrafiltration is preferably carried out at reduced temperatures to preserve the allergens, temperatures above the freezing temperatures up to 10° C. being useful, temperatures less than 4° C. being preferred.

The ultrafiltration equipment and filters employed are non-critical and can be those which are generally available commercially. Ultrafiltration procedures and equipment are described in *Remington's Pharmaceutical Sciences*, supra, pp 303–304 and 1397. Equipment such as MILLIPORE PELLICON CASSETTES (Millipore Corporation, Bedford, Mass.); AMICON stirred cells, fluid channel systems, and hollow fiber systems (Scientific Systems division, Amicon Corp. Danvers, Mass.) and NUCLEOPORE stirred cell and hollow fiber systems, Nucleopore Corp., Pleasanton, Cal. can be used. Suitable 1000 dalton and 100,000 dalton filters include MILLIPORE filters PCAC 00005, PTHK 00005, PSVP 00005 and PTHK 00001; NUCLEOPORE filters A1, C1, A100, C100, and F100 and AMICON filters YMZ and XM100A.

Ultrafiltration procedures and equipment therefore are described in *Separation Methods in Biochemistry*, Amicon publication No. 553; *Lab 50*, a Nucleopore publication, and *Laboratory products Catalogue* by Millipore.

The allergenic extract starting materials used in the process of this invention can be the conventionally obtained extracts of the plant and animal antigens which are the undenatured products which have heretofore been used for desensitization and diagnostic procedures. A full description of extraction procedures is presented in *Remington's Pharmaceutical Sciences*, supra, and the numerous patents listed above, the portions thereof directed to preparation of allergenic extracts being hereby incorporated by reference.

The source of the allergenic extract is subdivided if necessary to increase the surface area and rupture cell membranes to facilitate extraction. Materials containing little moisture may be repidly ground in household-type blenders. Materials containing much moisture may be disintegrated and extracted in a juice-extracting machine or less efficiently in a household type food or meat grinder. Materials such as animals hairs, feathers, kapok, silk and synthetic fibers must be cut into small fragments by cutting implements.

If the material contains fats and oils, it is defatted by extracting it with organic solvents. This is necessary to prevent emulsification during the aqueous extraction process and to obtain a clear product solution. Extraction solvents useful are those in which the fat is selectively soluble but in which the water soluble components are generally insoluble. Suitable solvents include ether, toluene, xylene and the like. In defatting, the material defatted is intimately mixed with successive portions of the organic solvent, and the organic phase is separated from the other materials. All pollens must be defatted. The extraction of materials to remove irritants (oils, resins and waxes) may require the use of multiple solvents.

In the extraction procedure, the active allergenic substances are removed from the solid materials in a solvent phase. The active allergen fractions, because they are soluble in alkaline solutions, are generally extracted with a buffered saline solution having a pH of about 8. For example, the extraction can be carried out by macerating the material to be extracted in the extracting solvent for 12 to 72 hours with shaking or other vibration. Extraction temperatures as high as 10° C. can be used, but preferred extraction temperatures are less than 4° C. The advantages of using a buffered extracting fluid are that it neutralizes both acids and alkalines, resisting a pH change from 8 which is the optimum pH for extraction. It also neutralizes acids and alkalines which might prove irritating in the final product.

After the material has been extracted, the solvent containing the active ingredients is separated from the inactive material by filtration or similar procedures. The extract can then be directly processed by the ultrafiltration procedures of this invention.

Suitable allergenic extracts for essentially all of the most common allergens are commercially available in adequate quality to be used as the starting material in the process of this invention. For example, such allergenic extracts are available from Hollister-Stier, a division of Cutter Laboratories, Inc.

In the preferred process of this invention, the source material can be allergenic extracts or the source material (pollen, danders or the like) of the extracts listed in the Examples, for example.

The product of the ultrafiltration step is then dried to a moisture content of less than one percent. The drying must be carried out without temperature elevation to preserve the allergen levels. Conventional vacuum drying or freeze-drying procedures are suitable, and the procedures and equipment generally used for freeze-drying can be used. Preferably the extract solution in vials is frozen to a temperature of −30° C. or below for 2 hours, and a vacuum of 20 torr or less is applied. The shelves in which the vials are supported is gradually warmed to 25° C. When the material has less than one percent moisture and reaches equilibrium (no significant weight loss after 2 hours), freeze drying is complete. Suitable equipment is described, for example, in *Remington's Pharmaceutical Sciences*, supra, pp 1483–1485, the contents of which are hereby incorporated by reference.

For a product to be used in desensitization procedures, the liquid product of the ultrafiltration is preferably fed directly into sealable vials, and the product can be freeze-dried in the vials in which they would be ultimately packaged. Alternatively, the solutions can be freeze-dried in bulk, and the vials subsequently filled with standard amounts. The containers are then sealed, preferably retaining the contents under vacuum.

We have found that treating the extracts with ionizing radiation is advantageously within the range of from about 0.5 to 2.5 megarads and preferably not more than 1.5 to increase stability. Radiation within this disage range may be carried out at room temperature or below or at elevated temperatures if so desired. The temperature at which radiation is carried out is not critical to the method of the invention. However, practical temperatures are within the range of from about minus 10° to about 50° C. Higher doses may degrade the allergenic compounds and reduce their activity or change their allergen profile.

It is possible, however, to employ higher doses of radiation without degrading the extracts under certain conditions. For example, this may be accomplished by first lowering the temperatures of the extracts to extremely low levels, i.e.; at or about the temperature of liquid nitrogen. In addition, if the extracts are exceptionally dry during radiation, for example having a moisture content of less than one percent by weight, radiation doses of up to 2.5 megarads will not significantly degrade them.

It may be observed from the above discussion that the dosage of ionizing rays may be varied to some extent particularly depending on the moisture level of the extracts. The lower the moisture level, the higher will be toleration to sterilizing doses without degradation of the allergens.

Irradiation as described about may also be carried out advantageously in the absence of oxidizing agents, i.e., in an atmosphere having an oxygen concentration which is reduced to such a degree that the quantity of oxygen molecules present is not more than sufficient to react during irradiation with any enzymes remaining in the allergen extracts following ultrafiltration. The reduction of the oxygen presence can be obtained by packaging the allergens under and in the presence of an inert gaseous atmosphere such as nitrogen or by the use of partial vacuum packing. The irradiation in the presence of nitrogen rather than an oxygen atmosphere reduces the secondary or "indirect" destructive effects of radicals generated in the presence of water or oxygen. There is only a "direct" effect of direct bombardment by the ionizing rays.

Gamma radiation produced by cobalt 60 is a preferred ionizing ray for employment in the method of the invention. Gamma radiation produced by cobalt 60 has a high penetrating ability and obviates the need for concern about the thickness of the allergen composition to be penetrated.

Suitable radiation apparatus include apparatus customarily used for applying ionizing rays to a wide variety of materials, including for example foodstuffs. These are so well-known that further description need not be given herein. Those skilled in the art will appreciate the techniques of ionizing ray application.

If the allergen is to be used on a solid support in a diagnostic procedure, the preformed support can be treated with the product of the ultrafiltration process or with reconstituted allergen from the drying step previously described.

The diagnostic support preferably has a solid waterinsoluble surface. The surface can be widely varied. The surface may take different forms, have different physical characteristics, can be of different chemical compositions and may be of one or more compositions as a mixture of compositions, coatings or laminates or combinations thereof. The surface may also be considered in accordance with its function. The surface serves as a base or substrate which will retain a discrete existance in the assay solution so as to be discernable from the medium and usually separable from the medium. The surface serves to support reagents bound to it so that they are incapable of diffusing through the solution independent of the surface. In addition, the surface acts as a support for the compounds conjugated with the materials bound to the surface, either as a base for a deposit layer or a support for covalent or non-covalent bonds. The surface is effectively non-fluid, discrete in that the surface is distinguishable from the liquid medium in which the surface is immersed, and provides a distinct base or foundation for supporting the compounds. The surface may exist in an electrostatically charged or uncharged form, being charged where such charges provide some advantage to the operation of a particular label system.

A wide variety of compounds can be employed as the solid support, the primary consideration being the binding of the reagents to the surface and the absence of interference with the reactions involved in the binding and use. A wide variety of organic and inorganic polymers, both natural and synthetic may be employed as the material for the solid support. Illustrative polymers include polyethylene, polypropylene, polybutylene, poly(4-methylbutylene), butyl rubber and other synthetic rubbers, silicone rubbers and silastic polymers, polyesters, polyamides, cellulose and cellulose derivatives (such as cellulose acetate, nitrose cellulose and the like), acrylates, methacrylates, vinyl polymers (such as polyvinyl acetate, polyvinyl chloride, polyvinylidene chloride, polyvinyl fluoride, and the like), polystyrene and styrene graft copolymers, rayon, nylon, polyvinylbutyrate, polyformaldehyde, etc. Other materials which can be employed as the insoluble support may include silica gel, silicon wafers, glass, paper, insoluble protein, metals, metaleoids, metal oxides, magnetic materials, semi-conductive materials, cermets or the like. In addition are included substances that form gels, such as proteins such as gelatins, lipopolysaccharides, silicates, agarose, polyacrylamides or polymers which form several aqueous phases such as dextrans, polyalkylene glycols (alkylene with 2 to 3 carbon atoms) or surfactants, e.g. amphiphilic compounds such as phospholipids, long chain (12–24 carbon atoms) alkyl amonium salts and the like.

The surface will usually be polyfunctional or be capable of being polyfunctionalized so as to allow for covalent bonding between the reagents and the surface. Functional groups which may be present on the surface and used for linking can include carboxylic acids, aldehydes, amino groups, cyano groups, ethylenic groups, hydroxyl groups, or mercapto groups and the like. The manner of linking a wide variety of compounds to the various surfaces is well known and is amply illustrated in the literature, for example, *Immobilized Enzymes*, Ichiro Chibata, Halsted Press, New York, 1978, and A. Cuatrecasas, *J. Bio. Chem.* 245 3059(1970).

The lengths of the linking group may vary widely depending upon the nature of the compound being linked, the effect of the distance between the linked compound and the surface on the linked compound's properties, the potential for cross-linking of the linked compound, and the like. The linking group may be a bond or have up to about 12, usually not more than 10 atoms in a chain. The linking group may be aliphatic, alicyclic, aromatic, heterocyclic, or combinations thereof. The total number of atoms of the linking group will be not more than about 20, usually not more than about 16 atoms other than hydrogen, which will be carbon, oxygen as oxy or oxo, both oxo-carbonyl and non-oxo-carbonyl, nitrogen as amino or amido, or sulfur as thio or thiono. Illustrative groups include methylenecarbonyl, succinimidyl, alpha-haloacetyl, thiomethylene, glycyl or polyglycyl, succindioyl, malediоyl, glutardialkylidene, methylenephenyldiazo, and ureido.

A preferred diagnostic support of this invention comprises an opaque (preferably black) polystyrene or styrene-(vinyl monomer) copolymer having the allergenic extract bound thereto by absorption, adsorption, ionic bonding, van der Waals adsorption, electrostatic bonding, or other non-covalent bonding, or covalent bonding. A particularly advantageous support for this procedure comprises a microtiter plate having a plurality of wells. The well surface or plastic cup inserts therein can constitute the allergenic extract support. Most advantageously, the microtiter plate or the well inserts are opaque to light so that excitation light applied to a well or fluorescense generated in response thereto does not reach or influence contents of the surrounding wells. With this system each well can be employed as a test system independent of the other wells.

For example, allergenic extracts of this invention can be applied by non-covalent bonding to a polystyrene microtiter well or polystyrene insert cup for a microtiter well by the following procedure. The polystyrene surface is washed with a cleaning liquid such as methanol. The extract, reconstituted in aqueous buffer solution is placed in the well or insert cup, incubated for 2 hours at room temperature, and removed. The well or insert cup is then rinsed with an aqueous sucrose or sorbitol solution and dried.

In one procedure for coating a polyethylene or polystyrene surface with allergenic extract, for example, the allergen is applied to the surface in a buffered solution containing an azide. A solution of allergenic extract having a concentration of from about 1 to about 100 micrograms of protein per ml is prepared from the allergenic extract in from about 0.005 to about 0.02 molar Tris-HCl, i.e., 2-amino-2-hydroxymethyl-1,3-propanediol-HCl. The Tris-HCl buffers the solution to a pH of from about 7.1 to about 9.5 together with from about 0.01 to about 0.05 weight percent sodium azide. This solution is then coated on the polymer surface and incubated at room temperature for from 6 to 72 hours and preferably from 12 to 48 hours. These coated surfaces are then washed with from about 0.005 to about 0.02 molar Tris-HCl at a pH of 6.9 to 8.4 plus from about 0.01 to about 0.05 weight percent sodium azide. It is preferred to utilize an 0.01 molar solution of Tris-HCl and 0.02 weight percent sodium azide buffered at a pH of 7.1 for both the incubation meduim and the washing medium. For additional details for methods of preparing allergenic extracts for coating or the affixing of such to tubes or other apparatus, reference can be made to the publication by C. M. Ling and L. R. Overby, "Prevalence of Hepatitis B. Antigen as Revealed by Direct Radioimmunoassay with $^{125}I$ Antibody," *Journal of Immunology*, Vol. 109, No. 4, October 1972. Although the coating method has been described with reference to a coated tube, the coating method may be utilized to prepare coated inserts, beads, or any apparatus for use with wells, etc. by dipping the inserts in the allergenic extract solution and following the remaining procedure.

In an alternate procedure, the support surface can first be coated with an inert protein. This procedure is described with respect to polyethylene or polystyrene tubes but is equally suitable for wells, beads, etc. To the reactive bottom part, in accordance with this procedure is attached an inert protein. The term inert protein means a protein which does not take part in the immunochemical reaction and does not adversely affect the biological substance. The proteins that can be used are well known to those skilled in the art. They include any proteinaceous material such as serum albumins or globulins obtained from various animal species or can be other uniform materials. Particularly preferred are bovine gammaglobulin and gelatin which are readily available. Desirably, the proteinaceous material employed should be sufficiently homogeneous so that an essentially continuous surface can be obtained by the use thereof. Such a surface is readily obtainable with the above proteins. allergenic extracts are then bonded to the inert proteins.

More specifically, the plastic surfaces are treated by a process which comprises (a) coating by adsorption the surface with an inert protein under adsorbing conditions, (b) attaching allergenic extract to the inert protein coating, (c) treating the coupled part with a stabilizing agent to stabilize the allergenic extract against denaturization, and (d) drying the reactive part under drying conditions that will not substantially denature the allergenic extract.

The amount of inert protein required to give optimum results is dependent on the nature of the inert protein, the surface and the allergenic extract. This amount is readily determinable by those skilled in the art. Typically, only a thin film e.g., at least one layer of molecules thick, of protein is attached to the surface. Generally, this is a sufficient amount to effect a uniform coating to which the biologically active substance may by attached.

The inert protein is readily attached to the surface to form a coating by spraying, soaking or, preferably by immersing the surface in an aqueous solution of inert protein, preferably an aqueous buffer solution under coating conditions. In this manner the protein is adsorbed to the surface. It is advantageous to use aqueous phosphate buffer solutions. Such buffers are described in U.S.P. XIX and are generally prepared using dipotassium hydrogen phosphate and potassium dihydrogen phosphate.

The inert protein is coated under adsorbing conditions which will not lead to denaturization of the protein. Specific pH and temperature conditions depend on the particular inert protein. Adsorbing conditions include conventional pH's, e.g. about 3 to 10 and conventional temperatures, e.g., about 20° C. to 30° C. While lower and higher application temperatures may be employed, for example as low as 4° C. and as high as 50° C., there is no significant advantage. In fact, at temperatures in excess of 50° C., the protein is generally denatured. At temperatures lower than 4° C. the protein is difficult to apply. For example, bovine gammaglobulin is coated generally at a pH of 5 to 7 optimally 6.4 at room temperature.

To facilitate attachment of the inert protein, the surface of the lower reactive part prior to attachment may be treated with solvents, surfactants, acids or bases. Surfactants, advantageously, sodium dodecyl sulfate, are utilized as detergents to clean the surface and make it wettable. If the polymers contain carboxyl groups on the surface, often it is desirable to treat them with a salt-forming base, e.g. KOH, to convert them to the salt form, thus giving them a negative charge which provides for enhanced electrical attraction and further enhancing adsorption. The base also helps to clean the surface. In another aspect, it is advantageous to make the charge distribution on the surface about equal to that of the inert protein to be applied. This is accomplished by washing the surface with an aqueous buffer solution having about the same pH as the coating solution containing the inert protein prior to coating.

The allergenic extracts may be attached by any suitable means. Such suitable means known to the art include adsorption, covalent binding, ionic binding and entrapment. It is preferred to attach the allergenic extract by covalent binding because it is easier to control the coupling reaction, and the product is more stable. Methods for chemically, i.e. covalently binding the allergenic extracts to the inert protein are disclosed in U.S. Pat. Nos. 3,553,310 and 3,639,558, which are incorporated herein by reference. A preferred method of covalent binding to inert protein is by first treating the protein with an aldehyde coupling agent, followed by application of the allergenic extract under conditions to permit the aldehyde to covalently bind to both the inert protein and the allergenic extract. Suitable aldehyde coupling agents are those which have either ethylenic unsaturation or a plurality of aldehyde groups, or both, such as acrolein, methacrolein and 2-butenal. Dialdehydes can be employed such as glutaraldehyde, propanedial and butanedial.

When one of these aldehydes is contacted with the surface of the inert protein, the protein is stabilized and polymerized by cross-linking, and aldehyde active moieties are fixed to the surfaces. These moieties are believed to be carbonyl groups and as such are highly reactive to the amine groups of allergenic extract since they form covalent bonds between the protein particles and the allergenic extract.

The aldehyde or ethylenically unsaturated coupling procedures can also be used to covalently bond the allergens to other surfaces having primary amino groups. For example, polylysine coated polystyrene can be coupled to allergens with glutaraldehyde.

Alternative to aldehydes, there may be used other coupling moieties such as compounds having two or more of the following reactive groups: azo, sulfonic acid or fluoro groups activated by nitro groups, azide, imine or reactive chloro groups connected to a ring having appropriate resonance structure. These reactive groups are capable of reacting with the primary amino, sulfylhydryl, carboxylic, hydroxyl and phenolic groups in the substances constituting the inert protein as well as the allergenic extract substances to be coupled thereto.

A representative list of such coupling agents is bis-diazobenzadine, disulfonic acid, tetraazo-p-phenylenediamine difluorodinitrobenzene, difluorodinitrophenylsulfone, carbodiimides, toluene diisocyanate, cyanuric chloride, dichlorotriazine, N-t-butyl-5-methylisoxazolium perchlorate. Carbodiimides which can be employed are N,N-dicyclohexylcarbodiimide, 1-ethyl-3(3-dimethylaminopropyl) carbodiimide hydrochloride, and 1-cyclohexyl-3(2-morpholinyl(4)-ethyl-carbodiimide)metho-p-toluene sulfonate.

Alternately the allergenic extract can be attached by adsorption according to the procedure described in U.S. Pat. No. 3,551,555.

Alternatively, the solid support surface can be coated with a material which will bind to the allergens through an isocyanate bond such as that provided by polyether isocyanate coatings (HYPOL-2000, W. R. Grace & Co., Lexington, Mass.).

Procedures for binding reagents to glass surfaces are known in the art and are described in U.S. Pat. No. 4,280,992, for example. Methods used of binding the allergenic extract to the glass are not critical. The frosted glass is preferred. Allergenic extract may be bound to the glass surface by physical or chemical methods. The latter are preferred when binding of a large amount of allergenic extract to the glass firmly and permanently is desired.

Binding by a physical method can be attained mainly by physical adsorption (van der Waals adsorption). Thus, the glass may be dipped in a solution of the allergenic extract and incubated; or allowed to stand, for an appropriate period of time to form physical binding. The solution can have a concentration of generally 0.001 to 40 g/100 ml preferably 0.01 to 0.1 g/100 ml. The dipping or immersion treatment can be carried out, for example, at a temperature of 0° to 45° C. for 1 to 48 hours.

As a suitable chemical method, the allergenic extract can be bound to glass surfaces, and preferably frosted glass surfaces, with the aid of a silane coupling agent and if necessary a cross-linking agent. There may be used any silane coupling agent having in its molicule both a functional group reactive with the glass and a functional group reactive with the allergenic extract and/or the cross-linking agent. Examples of suitable functional groups reactive with the glass include those reactive with a silanol group of the glass, and include, for example, alkoxysilyl groups (such as methoxyor ethoxy-substituted silyl groups), and the like. Examples of suitable functional groups reactive with the allergenic extract and/or the cross-linking agent are those reactive with amino, carboxyl and/or thiol group(s), and include, for instance, carboxyl, epoxy, haloalkyl (such as chloroethyl and chloropropyl), aldehyde, primary and secondary amino, thiol, isocyanate, carboxylate, imino and nitrile (or cyano) groups, and the like. More specifically, examples of suitable functional groups reactive with the amino group are carboxyl, epoxy, haloalkyl and aldehyde groups. Suitable functional groups reactive with the carboxyl group include, for example, primary and secondary amino, and epoxy groups. Suitable functional groups reactive with the thiol group include thiol, epoxy, haloalkyl and aldehyde groups, and the like. Illustrative examples of suitable silane coupling agents are:

(1) Silane coupling agents containing amino and alkoxysilyl groups: aminoalkyl-trialkoxysilanes (such as $\gamma$-aminopropyl-trimethoxysilane, $\gamma$-aminopropyl-triethoxysilane), N-($\beta$-aminoethyl)-$\gamma$-amino-propyl-methyl-dimethoxysilane, N-($\beta$-aminoethyl)-$\gamma$-aminopropyl-trimethoxysilane, and the like;

(2) Silane coupling agents containing thiol and alkoxysilyl groups: mercaptoalkyl-trialkoxysilanes (such as $\gamma$-mercoptopropyl-trimethoxysilane), and the like;

(3) Silane coupling agents containing epoxy and alkoxysilyl groups: $\gamma$-glycidoxypropyl-trimethoxysilane, triethoxysilylmethyl-ethylene oxide, $\beta$-(3,4-epoxycyclohexyl)-ethyl-trimethoxysilane, and the like.

(4) Silane coupling agents containing carboxyl and alkoxysilyl groups: 2-(trimethoxysilyl)propionic acid, and the like; and (5) Silane coupling agents containing haloalkyl and alkoxysilyl groups: $\gamma$-chloropropyl-trimethoxysilane, and the like.

In binding the allergenic extract to the glass, the silane coupling agent may be used with or without the cross-linking agent.

The crosslinking agent may be selected according to the kind of the silane coupling agent and the kind of the allergenic extract to be bound. There may be used any crosslinking agent which can crosslink the silane coupling agent with the allergenic extract. As such cross-linking agent there may be mentioned, those compounds that can cross-link the amino, carboxyl or thiol group of the silane coupling agent with the amino, carboxyl or thiol group of the immunologically active substance, such as those capable of producing a cross linkage between the thiol group and the thiol group, or between the amino group and the thiol group. Examples of suitable compounds which can crosslink between the amino group and the amino group are aliphatic dialdehydes (such as glyoxal, malonaldehyde, succinaldehyde, glutaraldehyde) and dichlorotriazines (such as 2-amino-4,6-dichloro-s-triazine), and the like. Suitable cross-linking agents between the thiol group and the thiol group are, for instance, dimaleimide compounds (such as N,N'-o-phenylenedimaleimide, N,N'-m-phenylenedimaleimide). Suitable cross-linking agents between the amino group and the thiol group are exemplified by maleimidocarboxyl-N-hydroxysuccinimide esters (such as m-maleimidobenzoyl-N-hydroxysuccinimide ester, and 4-(maleimidomethyl)cyclohexane-1-carboxyl-N -hydroxysuccinimide ester).

In producing the conjugates of this invention by chemical methods, there are two modes:

(1) binding the allergenic extract to the glass surface through the silane coupling agent, and (2) binding the allergenic extract to the glass surface agent.

According to the first mode, the conjugate can be produced, for example, by the following procedure. The silane coupling agent is first bound to glass by treating the latter with the silane coupling agent so as to make the agent react with the silanol group of the glass surface, and the resulting intermediate product is then reacted with the allergenic extract to form a linkage between the allergenic extract and the glass via the silane coupling agent. When an amino-containing silane coupling agent is used, it forms a peptide bond with the carboxyl group of the allergenic extract. The use of an epoxy-containing silane coupling agent causes an addition reaction with the amino, carboxyl or thiol group of the allergenic extract. The use of a thiol-containing silane coupling agent leads to formation of an S—S linkage with the thiol group of the allergenic extract. The use of an aldehyde-containing silane coupling agent leads to formation of a thioacetal or hemithioacetal with the thiol group of the allergenic extract. From the viewpoint of firm and permanent bonding of the allergenic extract and the glass, silane coupling agents which contain both an amino group and an alkoxysilyl group or both a carboxyl group and an alkoxysilyl group are preferred. The reaction generally occurring between the above silane coupling agent and the allergenic extract is a peptide formation reaction, and it is preferable to use on that occasion a water-soluble carbodiimide serving as dehydrating condensation agent, such as N-ethyl-N'-dimethylaminocarbodiimide, 1-ethyl-3-diisopropylaminocarbodiimide or 1-cyclohexyl-3-(2-morpholinoethyl)-carbodiimide.

According to the second mode, the conjugate can be produced, for example, by the following procedure. First the silane coupling agent is bound to the glass, then the silane-glass reaction product is reacted with the crosslinking agent, and finally the resulting intermediate is reacted with the allergenic extract. Judging from the view-point of firm and permanent binding of the allergenic extract with the glass, preferred silane coupling agents are amino- and alkoxysilyl-containing silane coupling agents, especially aminoalkyl-trialkoxysilanes, and preferred crosslinking agents are aliphatic dialdehydes, especially glutaraldehyde.

The amount of the silane coupling agent to be used in the chemical methods is not critical and can vary widely within the scope of this invention. The weight ratio of a solution of the silane coupling agent/the glass can be, for example, 30/100–1000/100, the solution having a concentration of usually 0.01 to 50 vol. % preferably 0.1 to 10 vol. %.

The amount of the crosslinking agent used in the second mode is not critical and can vary widely. The weight ratio of a solution of the crosslinking agent/the glass can be, for example, 30/100–1000/100, the solution having a concentration of usually 0.0001 to 50 wt. %, preferably 0.1 to 20 wt. %.

Procedures for binding the allergenic extract to the glass by the aid of the silane coupling agent and if necessary the crosslinking agent can be similar to those previously known except that the glass is used as carrier glass.

Thus, an illustrative example of such procedures, allergenic extract is bound to the glass surface via the silane coupling agent according to the first mode, is as follows. The frosted glass is well immersed in a solution of the silane coupling agent having a concentration of 0.01 to 50 V/V %(preferably 0.1 to 10 V/V %) in an organic solvent (such as acetone or toluene) at a temperature of 0° to 80° C. for 10 minutes to 24 hours, to allow the silane coupling agent to react with the glass. The so-treated glass is separated from the reaction mixture, and washed thoroughly in sequence with methanol and deionized water. To this frosted glass is added 10 to 1000 parts (preferably 50 to 300 parts) of a solution of the allergenic extract having a concentration of 0.001 to 40 g/100 ml (preferably 0.01 to 0.1 g/100 ml) per 100 parts of the frosted glass, and the reaction is allowed to proceed at about 0° to 40° C. for 10 minutes to 24 hours (preferably for 1 to 3 hours) so that the frosted glass and the allergenic extract may be bound together through the silane coupling agent. It is preferable to use a solution of a water-soluble carbodiimide at a concentration of 0.1 to 10 g/100 ml on the occasion of reacting the immunologically active substance with the frosted glass to which an amino- or carboxyl-containing silane coupling agent has been bound.

An illustrative example of procedures, wherein the immunologically active substance is to be bound to a frosted glass surface with the aid of the silane coupling agent and the crosslinking agent in accordance with the second mode, is as follows. The frosted glass is well immersed in a solution of the silane coupling agent having a concentration of 0.01 to 50 V/V % (preferably 0.1 to 10 V/V %) in an organic solvent (such as acetone or toluene) at a temperature of 0° to 80° C. for 10 minutes to 24 hours so that the silane coupling agent may react with and be bound to the frosted glass. Then the so-treated frosted glass is separated from the reaction mixture, and washed thoroughly in sequence with methanol and deionized water. This frosted glass is then well immersed in an aqueous solution of the crosslinking agent having a concentration of 0.001 to 50 W/W % (preferably 0.1 to 20 W/W %) at about 0° to 40° C. for 30 minutes to 10 hours, whereby the crosslinking agent is bound to the silane coupling agent that has been bound to the frosted glass. The frosted glass so treated is separated from the reaction mixture and washed thoroughly with deionized water. To the frosted glass is added 10 to 1000 parts (preferably 50 to 300 parts) of a solution of an allergenic extract, for example, having a concentration of 0.001 to 40 g/100 ml (preferably 0.01 to 0.1 g/100 ml) per 100 parts of the frosted glass, and the reaction is allowed to proceed at about 0° to 40° C. for 10 minutes to 24 hours (preferably for 1 to 3 hours), whereby the allergenic extract is bound to the frosted glass through the silane coupling agent and the crosslinking agent.

The allergenic extract-glass conjugates obtained according to this invention can contain usually 0.1 to 1000 $\mu$g, preferably 50 to 500 $\mu$g (per g. of frosted glass) of the allergenic extract bound to the glass. The amount of the silane coupling agent bound to frosted glass in the chemical method may be, for example, $10^{-5}$ to 1 $\mu$mole (preferably $10^{-4}$ to $10^2$ $\mu$mole) per g. of the glass. The amount of the crosslinking agent bound to the conjugate in the second mode is preferably stoichiometric amount to the crosslink the functional group of the silane coupling agent with the functional group of the allergenic extract but, may vary, for example, from 20% to 100% of the stoichiometric amount.

The allergenic extract-glass conjugates prepared in this manner are stable and can be stored for more than one year in a 0.01 M phosphate buffered physiological saline solution (pH 7.2) containing 1% sodium nitride and 1% bovine serum albumin at 4° C. for, instance.

Adsorbents useful in the process of the invention as solid supports for allergenic extracts are known in the art. Suitable materials are listed below:

ADSORBENTS

Non-ionic cellulose
   e.g., Whatman (Clifton, N.J., U.S.A.) types
      CF-1 ®, long fiber powder
      CF-11 ®, medium fiber powder
      CC-31 ®, microgranular powder
      CC-41 ®, microgranular powder
   e.g., Bio-Rad (Richmond, Cal., U.S.A.) types
      Cellex ® N-1, powder
      Cellex ® 410, powder
Silica gel
   e.g., Whatman type—SG 81, loaded paper; or Bio-Rad types—Bio-Sil ® A or Bio-Sil ® HA
Hydroxylapatite (Bio-Rad)
Alumina; acid, base, or neutral types (Bio-Rad)
Alumina C-gamma gel (Bio-Rad)
Calcium phosphate
Hydroxypropyl dextran
   e.g., Pharmacia (Piscataway, N.J., U.S.A.) type—Sephadex ® LH 20
Dextran (Pharmacia)
Dextran sulfate (Pharmacia)
Alkyl agaroses
   e.g., Pharmacia types—octyl-Sepharose ® Cl-4B or phenyl-Sepharose ® Cl-4B
   e.g., Miles Research Products (Elkhart, Ind., U.S.A.) types -$\omega$-amino alkyl agaroses
Lectin-agarose (Miles Research Products)
Poly-L-lysine agarose (Miles Research Products)
Plastics, e.g., polystyrene, polyethylene, and polypropylene

ANION EXCHANGE MATERIALS

Diethylaminoethyl (CEAE) cellulose
   e.g., Whatman types
      DE-1 ®, floc
      DE-11 ®, powder
      DE-22 ®, fibrous
      DE-23 ®, fibrous
      DE-32 ®, dry, microgranular
      DE-52 ®, wet, microgranular
      DE-81 ®, paper
   e.g., Bio-Rad type—Cellex ® D, fibrous
Diethylaminoethyl (DEAE) agarose
   e.g., Bio-Rad type—DEAE Biogel ® A
Diethylaminoethyl (DEAE) dextran
   e.g., Pharmacia type—DEAE Sephadex ®, bead
Aminohexyl-Sepharose ® 4B (Pharmacia)
Ecteola cellulose
   e.g., Whatman types
      ET-11 ®, powder
      ET-41 ®, powder (high purity)
      ET-81 ®, paper
   e.g., Bio-Rad type—Cellex ® E, fibrous
Triethylaminoethyl (TEAE) cellulose
   e.g., Bio-Rad type—Cellex ® T, fibrous
Diethyl-(2-hydroxypropyl)-amino (QAE) cellulose
   e.g., Bio-Rad type—Cellex ® QAE, fibrous
Diethyl-(2-hydroxypropyl)-amino (QAE) dextran
   e.g., Pharmacia type—QAE-Sephadex ®
Benzolyated diethylaminoethyl cellulose
   e.g., Bio-Rad type—Cellex ® BD, fibrous

CATION EXHANGE MATERIALS

Cellulose phosphate
   e.g., Whatman types
      P-1 ®, floc
      P-11 ®, powder
      P-41 ®, powder (high purity)
      P-81 ®, paper
Carboxymethyl cellulose
   e.g., Whatman types
      CM-1 ®, floc
      CM-11 ®, powder
      CM-22 ®, fibrous
      CM-23 ®, fibrous
      CM-32 ®, dry, microgranular
      CM-52 ®, wet, microgranular
      CM-82 ®, paper
   e.g., Bio-Rad type—Cellex ® CM, fibrous
Carboxymethyl dextran
   e.g., Pharmacia type—CM-Sephadex ®
Phosphoryl cellulose
   e.g., Bio-Rad type—Cellex ® P, fibrous
Carboxymethyl agarose
   e.g., Bio-Rad type—CM Biogel ® A
   e.g., Pharmacia type—CH-Sepharose ® 4B
Sulphopropyl dextran
   e.g., Pharmacia type—SP-Sephadex ®

Reagents formed by chemically coupling or combining the allergenic extract to polymeric carrier particles of varying particle size are well-known, e.g., U.S. Pat. Nos. 3,882,225; 3,957,931; 3,825,525; 3,629,558; 3,565,987, 3,553,310; 3,407,076; 3,236,732; 3,096,250; 4,092,114; 4,140,662; 4,210,723; 4,226,747; 4,259,313; 3,088,875; 3,766,013; 3,619,371; 3,809,613; 3,853,987; 3,963,441; 3,551,555; and 3,649,346. Netherlands Pat. No. 7,201,308; and British Pat. No. 1,257,263.

When covalent bonding of the allergenic extract to the polymer bead is desired, it is preferred to use for the bead a monomer which, after bead formation, retains a group which can react with amino, amido, or sulfonamido groups on the allergenic extract to be bound to the bead, e.g. chlorobenzyl, chloroacetyl, chloroethylcarbonyl, chloroethylsulfonyl, acryloyl, or vinyl-sulfonyl group.

Also the surface groups can be bonded to allergenic extract through bifunctional-linking groups reacted with the reactive bead surface group and with the allergenic extract.

The beads are usually prepared by polymerizing one or more vinyl monomers by standard procedures.

Suitable vinyl monomers which can be polymerized and/or copolymerized with each other in any proportions and/or with other monomers to yield the desired beads include monovinylidene carboxylic monomers, e.g., styrene, α-methylstyrene, ar-(t-butyl)styrene, ar-methylstyrene, ar,ar-dimethylstyrene, ar-chlorostyrene, ar-(t-amyl) styrene, ar-bromostyrene, ar-fluorostyrene, ar-cyanostyrene, ar-methoxystyrene, ar-ethylstyrene, ar-hydroxymethylstyrene, ar-ethoxystyrene, ar-chloro-ar-methylstyrene, ar, ar-dichlorostyrene, ar,ar-difluorostyrene, vinyl naphthalene, and other such emulsion polymerizable monomers having not more than 26 carbon atoms; esters of α,β-ethylenically unsaturated carboxylic acids which polymerize to form non-film forming polymers, e.g., methyl methacrylate, chloroethyl methacrylate, n-butyl methacrylate, ethyl methacrylate, isobutyl methacrylate, isopropyl methacrylate, phenyl methacrylate, butyl chloroacrylate, cyclohexyl chloroacrylate, ethyl chloroacrylate, methyl chloroacrylate, isopropyl chloroacrylate and other such esters capable of being polymerized to form hard polymers; α, β-ethylenically unsaturated esters of non-polymerizable carboxylic acids, e.g., vinyl benzoate, vinyl toluate ar-ethylbenzoate, allyl ar-ethylbenzoate, vinyl trimethylacetate, vinyl pivalate, vinyl trichloroacetate and other such monomers wherein the unsaturated moiety has from 2 to 14 carbon atoms and the acid moiety has from 2 to 12 carbon atoms; α, β-ethylencially unsaturated nitriles, e.g., such as nitriles having not more than 12 carbon atoms; other polymerizable vinyl monomers such as vinyl chloride, vinyl bormide and the like.

Key to successful treatment of allergic conditions is the accurate identification of the offending allergen and the titration of the affected animal to determine the desensitization dosage. In general, the reconstituted allergen extract is injected in sufficient quantity to cause major production of antigen-specific IgG and major production and/or activation of suppressor T lymphocytes. However, the quantity should not be sufficient to cause major allergic reaction and excessive antigen-specific IgE production. To the extent that antigen-specific IgE is produced at an increased level, it is critical that the IgG and suppressor IgE production is in such balance as to prevent allergic reaction.

The concentration and amount of the desensitization dosage are dependent upon many factors which are specific to the subject undergoing the allergic reaction. It is, therefore, necessary to titrate the patient to determine the proper dosage. A variety of standard techniques are available to carry out this procedure. Examples of traditional procedures are described in *Remington'Pharmaceutical Sciences*, supra, pp 1344–1352, the entire contents of which are incorporated herein by reference. The cutaneous or scratch test is performed by scarifying or making small abrasions on the skin of the patient and applying a small amount of the concentrated antigen. A positive reaction is indicated by a hive-like swelling and redness at the point of application, and is known clinically as a "wheal and flare" reaction. The reaction occurs in allergic individuals usually within 15 to 20 minutes. The size and appearance of the reaction provides a measure of the degree of sensitivity. Intracutaneous or intradermal testing is accomplished by injecting the allergenic material between layers of skin and observing the reaction. This test is more sensitive than the scratch test. Patch testing is a diagnostic procedure in which a small square of gauze or blotting paper, impregnated with allergen, is applied directly to the skin in order to elecit symptoms of allergic contact dermatitis. A reading is taken after 48 hours.

By simultaneously applying a variety of allergens to selected skin areas, those causing allergic response can be identified, and the focus can be narrowed to those allergens involved in an allergic reaction. The targeted allergens can be applied in a serial fashion, that is, can be applied in graduated and increased doses so as to identify the concentration-sensitivity relationship. For a more sensitive method, allergen attached to a solid support such as spherical beads, paper discs or the surface of a well in a microtiter plate as described above can be used. When the patient's serum is mixed with the allergen-labeled disc or beads, IgE with specific affinity for the allergen binds to the allergen on the paper or bead surface. All non-specific IgE is removed by washing the disc or beads. Labeled anti-IgE can then be added, and after the appropriate incubation and washings, the label level is measured. The label level is correlated to the amount, if any, of allergen-specific IgE existing in the patient serum and, thereby, the degree of allergen sensitivity. To apply these systems, it is necessary to have special anti-IgE and allergen marked support materials and to label the anti-IgE used in the second incubation step.

In view of the wide range of patient sensitivity and degree of allergic reaction, a dosage range for desensitizing treatment cannot be quantitatively predicted with accuracy. In general, the antigenic compositions of this invention are applied by standard procedures. They can be applied by injection intradermally, subcutaneously, intramuscularly, or administered orally, by inhalation, rectally or by other accepted means. The antigen composition is administered in a quantity of from 0.1 to 10,000 micrograms of antigen.

After identification of the offending allergen, hyposensitization immunotherapy procedures of this invention are employed. The procedure involves injecting into the host gradually increased doses of the composition of this invention, usually to maximum tolerated doses (doses not giving rise to major allergic response), at varying intervals in an attempt to develop IgG antibody protection against the agents and to increase the specific suppressor T lymphocyte activity. Exact mechanisms of this process are not fully understood. Booster injections to maintain the requisite IgG and suppressor T lymphocyte levels are required at intervals of one to four weeks. Usually the doses required for booster injections are substantially greater than the maximum dose required for control of the initial allergic reaction.

The injectable composition of this invention is an aqueous composition which contains one or more allergens which are substantially free from impurities, in combination with one or more physically acceptable, non-toxic excipients. For the injectable formulations, the concentration of allergen material is not critical and is determined by the dose needed per injection. In general, allergen concentrations of from 10 to 100,000 micrograms per ml can be used in the injectable composition.

The composition of this invention is used as an aqueous formulation. Certain aqueous vehicles are recognized officially because of their valued use in parenteral formulations. Often they are used as isotonic vehicles to which the antigen concentrate can be added at the time of administration. The additional osmotic effect of the allergen may not be enough to produce any discomfort when administered. These vehicles include Sodium Chloride Injection, Ringer's Injection, Coca's Solution, Evan's Solution, Dextrose Injection, Dextrose and Sodium Chloride Injection and Lactated Ringer's Injection.

The injectable compositions must be free from microbial and particulate contamination, free from pyrogen contamination and to the extent they contain suspended solids, should be easily dispersed to form an injection mixture having a uniform concentration.

The excipients added can be those generally used for parenteral compositions. In general, these fall in the categories of isotonic salts, anti-microbial agents, buffers and antioxidants.

Any water-soluble, non-toxic salts generally used in adjusting the tonicity of parenteral solutions can be used. Sodium chloride is most commonly used. Other suitable salts are listed in *Remington's Pharmeceutical Sciences*, supra, pp 1405–1412 together with their isoosmotic concentrations, the content of which are hereby incorporated by reference.

Antimicrobial agents in bacteriostatic or fungistatic concentrations can be added, particularly to preparations contained in multi-dose containers. They must be present in adequate concentration at the time of use to prevent the multiplication of microorganisms inadvertently introduced into the preparation while withdrawing a portion of the contents with a hypodermic needle and syringe. The compounds generally approved and the concentration limit prescribed for each are set forth in the United States Pharmacopeia (USP). Suitable antimicrobial agents include phenylmercuric nitrate, thimerosal 0.01%, benzethonium chloride and benzalkonium chloride 0.01%, phenol or cresol 0.5%, and chlorobutanol 0.5%. These concentrations are stated as those in the parenteral composition. Phenylmercuric nitrate is frequently employed in a concentration of 0.002%. Methyl p-hydroxybenzoate 0.18% and propyl p-hydroxybenzoate 0.02% in combination, and benzyl alcohol 2% are also suitable.

The buffers are used primarily to stabilize a solution against the chemical degradation that would occur if the pH changed appreciably. Buffer systems employed should normally have as low a buffer capacity as feasible in order not to disturb significantly the body's buffer systems when injected. In addition, the buffer range and the effect of the buffer on the activity of the antigen is of concern. The acid salts most frequently used as buffers are water-soluble salts such as sodium, potassium, and ammonium citrates, acetates and phosphates.

Antioxidants can be used to preserve allergens which deteriorate during prolonged storage due to oxidation. Suitable antioxidants include sodium bisulfite 0.1%, acetone sodium bisulfite, sodium formaldehyde sulfoxylate, and thiourea. The sodium salt of ethylenediaminetetracetic acid chelates metal ions which would otherwise catalyze the oxidation reaction, and it will, therefore, sometimes enhance the activity of an antioxidant.

The anhydrous allergenic extract of this invention is a stable, free from water (less than one percent water) and impurities. It can be free of excipients or it can contain pharmaceutically acceptable, non-toxic excipients which, when reconstituted with water or with normal parenteral solutions yield a composition suitable for parenteral administration according to the method of this invention. The amounts of antimicrobial agents and antioxidants present, if any, should yield a final concentration in a parenteral solution which falls within the range of those concentrations for each agent approved by the USP. Since the activities of the antimicrobial compounds and antioxidants are specific to each selected compound, a general overall range cannot be stated, the range being specifically selected based upon each drug in light of the USP-approved concentrations.

In general, the stable allergen extract contains from 0.01 to 99.9 weight percent allergenic compounds. It can also optionally contain from 0 to 2 and preferably from 0.1 to 0.5 weight percent antimicrobial composition, and from 0 to 5 and preferably from 0.1 to 2 weight percent antioxidant. If the dry concentrate is to be mixed with a buffered isotonic parenteral solution to form the final parenteral injectable composition, it is unnecessary to have buffers and isotonic salts present in the dry concentrate. However, if the dry concentrate is to be reconstituted with distilled water, then it can contain from 0.1 to 5 and preferably from 0.5 to 2 weight percent buffering compound such as monobasic potassium phosphate, dibasic sodium phosphate, sodium bicarbonate or the like and a sufficient quantity of an isotonic salt such as sodium chloride to provide an isotonic solution.

The parenteral composition for injection can be prepared from a dry concentrate, as indicated above, by mixing the concentrate with standard parenteral solutions or, alternatively, it can be reconstituted with distilled water. Typical standard parenteral solutions include Buffered Saline, Coca's Solution, Glycerinated Coca's Solution, Isotonic Sodium Chloride Solution, Sodium Bicarbonate Solution, Glycerin Saline Solution, Alcohol Saline Solution, Dextrose Solution 5%, and Dextrose Saline Solution. These solutions and their preparation are described in most pharmaceutical handbooks such as *Remington's Pharmaceutical Sciences*, supra, pp 1345 and 1461–1487, which are hereby incorporated by reference.

STORAGE STABILITY TEST

Vacuum sealed vials containing 100,000 Activity Units of allergen (FDA recommended standard) are prepared.

1. At day zero 3 vials of allergen are reconstituted and tested in triplicate by RAST inhibition. At the same time 6 vials are placed in a 38° C. incubator, 6 vials at 22° C. (room temperature), 12 vials in a 28° C. incubator and 12 vials in a 33° C. incubator.

2. After 8 days, 3 vials from the 38° C., 33° C. and 28° C. incubators are reconstituted and tested in triplicate by RAST inhibition. Six vials from 22° C., 28° C. and 33° C. incubators are reconstituted and returned to the 22° C., 28° C. and 33° C. incubators.

3. After 2 more days, 3 previously reconstituted vials from 22° C., 28° C. and 33° C. incubators are tested in triplicate by RAST inhibition.

4. After 15 days total (7 for the reconstituted vials), 3 vials from the 38° C., 33° and 28° C. incubators are reconstituted and tested in triplicate by RAST inhibition. Three vials from 22° C., 28° C. and 33° C. incubators which have been previously reconstituted are also tested in triplicate by RAST inhibition.

The RAST test is described by T. Foucard et al, *Int. Arch. Allergy Appl. Immunol.*, 43, 360; G. J. Gleich et al, *J. Allergy Clin. Immunol.*, 53, 158; and L. Yman, *DEV. Biol. Standard.*, 29, 151; the entire contents of which are hereby incorporated by reference.

In the test the allergens are reconstituted with 5 ml Delveccio's PBS solution having the following composition without breaking the seal.
Potassium Chloride: 0.20 g/l
Potassium dihydrogen phosphate: 0.20 g/l
Sodium Chloride: 8.00 g/l
Disodium phosphate (Na$_2$HPO$_4$.7H$_2$O): 2.16 g/l
Distilled water: qs 1.00 l This invention is further illustrated by the following specific but non-limiting examples.

EXAMPLE 1

Short Ragweed Extract

Defatting: To a 5 l round bottom flask of a Soxhlet extractor was added 4000 ml of diethyl ether and boiling stones. A 313.16 g quantity of pollen from Short Ragweed (*Ambrosia artemisiifolia*) in an extraction thimble was placed in the Soxhlet extractor. The water flow through the condenser was begun, and the ether heated under reflux (without excessive boiling) until return liquid was clear. The pollen was spread evenly on a paper tray and air-dried until no detectable ether was present to yield 278.46 g of defatted pollen.

Extraction: To an extraction vessel was added 133.4 g of defatted Short Ragweed pollen and 1334 of water (U.S.P. grade WFI). The extraction was continued for 17.5 hr at 4° C., and the solids were removed by passing the mixture through a cellulose filter paper.

Filtration and Ultrafiltration: The filtrate was clarified by passing it through a 0.5 micron filter. It was then passed through a 100,000 dalton ultrafilter. The ultrafiltrate was then ultrafiltered with a 1000 dalton ultrafilter yielding 420 ml of solution having components in the 1000–100,000 dalton range.

Lyophilization: The solution was then placed in vials, each vial containing the equivalent of 5 ml of 1:10 wt/vol equivalent extract, i.e. sufficient solution to yield 100,000 Allergy Units (FDA recommended standard). The vials were frozen to −30° C. for 2 hours, vacuum was applied, the lyophilizer shelf was gradually heated to 25° C., and the freeze-drying was continued until constant weight was achieved to yield vials containing 100,000 units of desiccated Short Ragweed pollen extract having a moisture content of less than one wt. %.

EXAMPLE 2

Pollen Extracts

Repeating the procedure of Example 1 but replacing the perennial ryegrass pollen with the following pollens yielded the corresponding allergenic extracts having no components with molecular weights outside the 1000 to 100,000 dalton range and having a moisture content of less than one percent.
Bermuda Grass — *Cynodon dactylon*
Western Ragweed — *Ambrosia psilostachya*
Perenneal Rye Grass — *Loluim perrene*
Johnson Grass — *Sorghum haleplese*
Timothy Grass — *Phleum prateuse*
Corn — *Zea mays*
Mountain Cedar — *Juniperus sabinoides*
English Plautain — *Plantago lanceolata*
White Ash — *Fraximus americana*
White Oak — *Quercus alba*
Box Elder — *Aces negundo*
White Alder — *Alnus rhombifolia*
American Elm — *Ulnus americana*
Bahia Grass — *Paspalum notatum*
Sagebrush — *Artemesia tridentata*
Orchard Grass — *Dactylis glomerata*
Russian Thistle — *Salsola kali* (pestifer)
Meadow Fescue — *Festuca elatior*
Olive — *Olea europaea*
Black river Birch — *Betula nigra*
Lamb's Quarters — *Chenopodium album*

EXAMPLE 3

Pollen Extracts

Repeating the procedure of Example 1 with the following tree pollens, grass pollens and weed pollens yields the corresponding extracts:

Tree pollens—Acacia—*Acacia longifolia*; Acacia, Bailey's—*Acacia baileyana*; Ailanthus (See Tree of Heaven)—*Ailanthus altissima*; Alder, Mountain (Tag) (Slender)—*ainus tenuifolia/incana*; Alder, Red (Oregon-)—*Alnus rubra*; Alder, Sitka—*Alnus sinuata*; Almond—*Prunus amygdalus*; Apple—*Pyrus malus (Malus pumila)*; Apricot—*Prunus armeniaca*; Arbor Vitae, Oriental (Ornamental)—*Thuja orientalis*; Ash, Arizona (Velvet)—*Fraxinus velutina*; Ash, Blake—*Fraxinus nigra*; Ash, Green (Red)—*Fraxinus pennsylvanica*; Ash, Oregon—*Fraxinus oregona* (latifolia); Aspen—*Populus tremuloides*; Bayberry (Sweet Gale)—*Myrica gale*; Beech, American—*Fagus grandifolia*; Birch, Cherry—*Betula lenta*; Birch, Paper—*Betula papyrifera*; Birch, Spring—*Betula fontinalis*; Birch, White (Weeping)—*Betula pendula*; Birch, Yellow—*Betula lutea*; Blue Beech (Am. Hornbeam)—*Carpinus carolineana*; Bottle Brush—*Callistemon citrinus*; Butternut—*Juglans cinerea*; Carob Tree—*Ceratonia siliqua*; Cedar, Deodar—*Cedrus deodora*; Cedar, Giant—*Thuja plicata*; Cedar, Incense—*Linocedrus decurrens*; Cedar, Japanese—*Cryptomeria japonica*; Cedar, Port Orford (Lawson Cypress)—*Chamaecyparis lawsoniana*; Cedar, Red—*Juniperus virginiana*; Cedar, Rocky Mountain—*Juniperus scopulorum*; Cedar, Salt (Tamarisk)—*Tamarix gallica*; Cedar, White—*Thuja occidentalis*; Cherry, *Prunus cerasus*; Chestnut, American—*Castanea dentata*; Chestnut, Horse—*Aesculus hippocastanum*; Cottonwood, Black (Poplar, Western Balsam)—*Populus trichocarpa*; Cottonwood, Common—*Populus deltoides*; Cottonwood, Fremont—*Populus fremontii*; Cypress, Arizona—*Cupressus arizonica*; Cypress, Bald (White)—*Taxodium distichum*; Cypress, Italian—*Cupressus sempervirens*; Cypress, Monterey—*Cupressus macrocarpa*; Elderberry—*Sambucus glauca*; Elm, Cedar (Fall Blooming-)—*Ulmus crassifolia*; Elm, Chinese—*Ulmus parvifolia*; Elm, Siberian—*Ulmus pumila*; Elm, Slippery—*Ulmus fulva* (rubra); Eucalyptus (Blue Gum)—*Eucalyptus globulus*; Fir, Douglas—*Pseudotsuga menziesii*; Fir, Red (Noble)—*Abies nobilis* (procera); Fir, White—*Abies concolor*; Gum, Sweet—*Liquidambar styraciflua*; Hackberry—*Celtis occidentalis*; Hazelnut, American—*Corylus americana*; Hemlock, Eastern—*Tsuga canadensis*; Hemlock, Western—*Tsuga heterophylla*; Hickory, Shagbark—*Carya ovata*; Hickory, Shellbark—*Carya laciniosa*; Hickory, White—*Carya tomentosa*; Ironwood (Hop-Hornbeam)—*Ostrya virginiana*; Juniper, California—*Juniperus californica*; Juniper, Chinese—*Juniperus chinensis*; Juniper, Oneseed—*Juniperus monosperma*; Juniper, Pinchot—*Juniperus pinchotti*; Juniper, Utah—*Juniperus osteosperma (Juniperus utahensis)*; Juniper, Western—*Juniperus occidentalis*; Lilac—*Syringa vulgaris*; Linden (Basswood)—*Tilia americana*; Locust, Black—*Robinia pseudoacacia*; Maple, Big-Leaf (Coast-)—*Acer macrophyllum*; Maple, Hard (Sugar)—*Acer saccharum*; Maple, Red—*Acer rubrum*; Maple, Soft (Silver-)—*Acer saccharinum*; Melaleuca (Punk Tree)—*Melaleuca leucadendron*; Mesquite—*Prosopis juliflora*; Mock Orange, Wild (Syringa)—*Philadelphus lewisii*; Mulberry, Paper—*Broussonetia papyifera*; Mulberry, Red—*Morus rubra*; Mulberry, White—*Morus alba*; Oak, Arizona (Gambel)—*Quercus gambelii*; Oak, Arizona Scrub (Canyon)—*Quercus chrysolepsis*; Oak, Black (Yellow)—*Quercus velutina*; Oak, Black Jack—*Quercus marilandica*; Oak, Bur—*Quercus macrocarpa*; Oak, California Black—*Quercus kelloggii-californica*; Oak, California Scrub—*Quercus dumosa*; Oak, Coast Live—*Quercus agrifolia*; Oak, Engelmann—*Quercus engelmanii*; Oak, Garry (Western White)—*Quercus garryana*; Oak, Holly—*Quercus ilex*; Oak, Interior Live—*Quercus wislizenii*; Oak, Post—*Quercus stellata*; Oak, Red—*Quercus rubra*; Oak, Swamp (Pin)—*Quercus palustris*; Oak, Valley—*Quercus lobata*; Oak, Virginia Live—*Quercus virginiana*; Oak, Water—*Quercus nigra*; Orange—*Citrus sinensis*; Osage Orange—*Maclura pomifera*; Palm, Date—*Phoenix dactylifera*; Palm, Dwarf—*Chamaerops humulis*; Palm, Canary Island Date (Ornamental)—*Phoenix canariensis*; Palm, Queen—*Cocos plumosa*; Peach—*Prunus persica*; Pear—*Pyrus communis*; Pecan—*Carya pecan*; Pepper Tree, California—*Schinus molle*; Pepper Tree, Brazilian—*Schinus terebinthifolius*; Pine, Australian (Beefwood-)—*Casuarina equisetifolia*; Pine, Austrian—*Pinus nigra*; Pine, Canary Island—*Pinus canariensis*; Pine, Digger—*Pinus sabiniana*; Pine, Loblolly—*Pinus taeda*; Pine, Lodgepole—*Pinus contorta*; Pine, Monterey—*Pinus radiata*; Pine, Pinyon—*Pinus edulis*; Pine, Red (Norway)—*Pinus resinosa*; Pine, Shortleaf—*Pinus echinata*; Pine, Virginia Scrub—*Pinus virginiana*; Pine, Western Yellow (Ponderosa)—*Pinus ponderosa*; Pine, White (Eastern)—*Pinus strobus*; Pine, White (Western-)—*Pinus monticola*; Plum (Prune)—*Prunus domestica*; Poplar, Balsam—*Populus balsamifera*; Poplar, Lombardy—*Populus nigra-italica*; Western Balsam (See Cottonwood, Black) *Populus trichocarpa*; Poplar, White—*Populus alba*; Privet—*Ligustrum spp.*; Redwood—*Sequoia sempervirens*; Russian Olive—*Elaeagnus angustifolia*; Spruce, Red—*Picea rubens*; Spruce, Sitka—*Picea sitchensis*; Sycamore, American (Eastern)—*Platanus occidentalis*; Sycamore, Mapleleaf—*Platanus acerifolia*; Sycamore, Western—*Platanus racemosa*; Tamarack (Larch)—*Larix occidentalis*; Tamarisk (See Cedar, Salt)—*Tamarix gallica*; Tree of Heaven—*Ailanthus altissima*; Walnut, Arizona—*Juglans rupestris*; Walnut, Black—*Juglans nigra*; Walnut, Hind's California Black—*Juglans hindsii*; Walnut, So. California Black—*Juglans californica*; Walnut, English—*Juglans regia*; Willow, Arroyo—*Salix lasiolepis*; Willow, Black—*Salix nigra*; Willow, Pussy—*Salix discolor*; Willow, Red—*Salix laevigata*; Willow, Yellow—*Salix lasiandra*.

Grass and Weed pollens—Barley, Cultivated—*Hordeum vulgare*; Bent Grass, Colonial—*Agrostis tenuis*; Bluegrass, Annual—*Poa annua*; Bluegrass, Canada—*Poa compressa*; Bluegrass, kentucky (June)—*Poa pratensis*; Bluegrass, Sandberg—*Poa sandbergii*; Brome Broncho-Ripgut—*Bromus rigidus*; Brome, California—*Bromus carinatus*; Brome, Cheat—*Bromus secalinus*; Brome, Smooth—*Bromus inermis*; Brome, Soft Cheat—*Bromus mollis*; Bunch, Blue (Northwestern Bunch)—*Agropyron spicatum*; Canarygrass—*Phalaris canariensis*; Canarygrass, Reed—*Phalaris arundinacea*; Fescue, Red—*Festuca rubra*; Grama Grass, Blue (Side Oats)—*Bouteloua gracilis*; Koeler's Grass (Western Junegrass)—*Koeleria cristata*; Lovegrass, Hawaiian—*Eragrostis variabilis*; Oats, Common Cultivated—*Avena sativa*; Oatgrass, Tall—*Avena elatior* (Arrhenatherum elatius); Quack Grass—*Agropyron repens*; Redtop—*Agrostis alba*; Rye, Cultivated—*Secale cereale*; Ryegrass, Alkali—*Elymus triticoides*; Ryegrass, Giant Wild—*Elymus cinereus*; Ryegrass, Italian—*Lolium multiflorum*; Ryegrass, Western—*Elymus glaucus*; Salt Grass—*Distichlis stricta*; Sorghum, Common Cultivated—*Sorghum vulgare*; Sudan Grass—*Sorghum vulgare* var. sudanese; Sweet Vernal grass—*Anthoxanthum odoratum*; Velvetgrass—*Holcus lanatus*; Wheat, Cultivated—*Triticum aestivum*; Wheatgrass, Crested—*Agropyron cristatum*; Wheatgrass, Western—*Agropyron smithii*; Alfalfa—*Medicago sativa*; Aster—*Aster sinensis*; Balsam Root—*Balsamorhiza sagittata*; Bassia—*Bassia hyssopifolia*; Beach Bur—*Franseria bipinnatifida*; Burro Brush (Greasebush)—*Hymenoclea salsola*; Careless Weed—*Amaranthus palmeri*; Castor Bean—*Ricinus communis*; Cattail, Broadleaf—*Typha latifolia*; Clover, Red—*Trifolium pratense*; Clover, Sweet, Yellow—*Melilotus officinalis*; Clover, White (Dutch)—*Trifolium repens* (album); Cocklebur, Common—*Xanthium strumarium*; Cocklebur, Spiny—*Xanthium spinosum*; Cosmos—*Cosmos bipinnatus*; Daffodil—*Narcissus pseudonarcissus*; Dahlia—*Dahlia pinnata x coccinea*; Daisy/ Chrysanthemum (Oxeyed Daisy)—*Chrysanthemum leucanthemum*; Dandelion—*Taraxacum officinale*; Dock, Bitter—*Rumex obtusifolius*; Dock, Yellow (Curly)—*Rumex crispus*; Dog Fennel (Mayweed-)—*Anthemix cotula*; Fireweed, Alaska—*Epilobium angustifolium*; Gladiolus—*Gladiolus Xhortulanus*; Goldenrod—*Solidago spp*; Greasewood—*Sarcobatus vermiculatus*; Hemp—*Cannabis sativa*; Hops—*Humulus lupulus*; Hopsage—*Grayia spinosa*; Iodine Bush (Burro Weed)—*Allenrolfea occidentalis*; Kochia (Mex. Firebush)—*Kochia scoparia*; Lily, Easter—*Lilum longiflorum*; Marigold—*Tagetes patula*; Marshelder, Burweed (Giant Poverty)—*Iva Xanthifolia*; Marshelder, Narrowleaf (August)—*Iva angustifolia*; Marshelder, True (Rough)—*Iva ciliata*; Mexican Tea—*Chenopodium ambrosioides*; Mustard, Black—*Brassica nigra*; Mustard, Common Yellow—*Brassica campestris*; Nettle—*Urtica dioica* (gracilis); Pickleweed—*Salicornia ambigua*; Pigweed, Rough Redroot—*Amaranthus retroflexus*; Pigweed, Spiny—*Amaranthus spinosus*; Poppy, California—*Eschoscholzia californica*; Povertyweed, Small—*Iva axillaris*; Rabbit Brush—*Chrysothamnus nauseosus*; Rabbit Bush (Bur Ragweed)—*Franseria deltoides*; Ragweed, Canyon—*Franseria ambrosioides*; Ragweed, Desert—*Franseria dumosa*; Ragweed, False—*Franseria acanthicarpa*; Ragweed, Giant—*Ambrosia trifida*; Ragweed, Short—*Ambrosia artemisiifolia* (elatior); Ragweed, Silver—*Dicoria canescens*; Ragweed, Slender—*Franseria tenuifolia*; Ragweed, Southern—*Ambrosia bidentata*; Rose—*Rosa multiflora*; Sagebrush, Coast—*Artemisia californica*; Sagebrush, Green (Tarragon-)—*Artemisia dracunculus*; Sagebrush, Mugwort—*Artemisia vulgaris heterophylla*; Sagebrush, Pasture (Carpet-)—*Artemisi frigida*; Sagebrush, Sand Dune—*Artemisia pycnocephala*; Sagebrush, White (Prairie)—*Artemisia ludoviciana*; Saltbush, Annual—*Atriplex wrightii*; Scale, All—*Atriplex polycarpa*; Scale, Bract—*Atriplex serenana bracteosa*; Scale, Brewers—*Atriplex lentiformis breweri*; Scale, Lens—*Atriplex lentiformis*; Scale, Red—*Atriplex rosea*; Scale, Silver (Fogweed)—*Atriplex argentea ex-*

*pansa*; Scale, Spear—*Atriplex patula hastata*; Scale, Wing (Shad)—*Atriplex canescen*; Scotch Broom—*Cytisus scoparius*; Sea Blite, California—*Suaeda californica*; Sedge—*Carex barbara*; Sheep Fat—*Atriplex confertifolia*; Sheep Sorrel—*Rumex acetosella*; Snapdragon—*Antirrhinum majus*; Suaeda (See Sea Blite); Sugar Beet—*Beta vulgaris*; Sunflower—*Helianthus annuus*; Waterhemp, Western—*Acnida tamariscina*; Winter Fat—*Eurotia lanata*; Wormseed (Jerusalem Oak)—*Chenopodium botrys*; Wormwood, Absinthe—*Artemisia absinthium*.

EXAMPLE 4

Epidermals and Glandular Elements

Repeating the extraction, filtration, ultrafiltration and lyophilization procedures of Example 1 but replacing the defatted Short Ragweed with cat hair and dander and with dog hair yielded the corresponding extracts.

EXAMPLE 5

Epidermals and Glandular Elements

Repeating the extraction, filtration, ultrafiltration and lyophilization procedures of Example 1 with the following epidermals and glandular elements yields the corresponding extracts: Camel Hair & Dander; Cattle Hair & Dander; Deer Hair & Dander; Feathers, Chicken; Feathers, Duck; Feathers, Goose; Feathers, Parakeet; Feathers, Pigeon; Feathers, Turkey; Fox Fur; Gerbil Hair & Epithelium; Glue, Fish; Goat Hair & Dander; Guinea Pig Hair & Dander; Hamster Hair & Epithelium; Hog Hair & Dander; Horse Hair & Dander; Human Hair; Mink Fur; Mohair; Monkey Hair & Epithelium; Mouse Hair & Epithelium; Poodle Hair & Dander; Pyrethrum; Rabbit Hair & Epithelium; Rat Hair & Epithelium; Seal Fur; Wool, Sheep.

EXAMPLE 6

Alternaria Tenuis Extract

Repeating the extraction, filtration, ultrafiltration and lyophilization procedures of Example 1 but replacing the defatted Short Ragweed with the mold Alternaria tenuis yielded the corresponding extract.

EXAMPLE 7

Mold and Smut Extracts

Repeating the extraction, filtration, ultrafiltration and lyophilization procedures of Example 1 with the following molds and smuts yields the corresponding extracts:

Molds—*Aspergillus clavatus; Aspergillus fumigatus; Aspergillus glaucus; Aspergillus nidulans; Aspergillus niger; Aspergillus restrictus; Aspergillus sydowi; Aspergillus terreus; Botrytis cinerea; Candida albicans; Cephalosporium acremonium; Cephalothecium*(Trichothecium) *reseum; Chaetomium globosum; Cryptococcus terreus; Cunninghamella elegans; Curvularia spicifera; Dematium nigrum; Epicoccum nigrum; Epidermophyton floccosum; Fomes rimosus; Fusarium vasinfectum; Geotrichum candidum; Helminthosporium maydis; Helminthosporium; Hormodendrum* (Cladosporium); *Monilia sitophila; Mucor racemosus; Mycogone sp.; Neurospora crassa; Nigrospora sphaerica; Oidiodendrum sp.; Paecilomyces varioti; Penicillium artramentosum; Penicillium biforme; Penicillium carminoviolaceum; Penicillium chrysogenum; Penicillium digitatum; Penicillium expansum; Penicillium glaucum; Penicillium intricatum; Penicillium luteum; Penicillium notatum; Penicillium roqueforti; Penicillium roseum; Phoma herbarum; Pleospora sp.; Poria sp.; Pullularia pullulans; Rhizopus nigricans; Rhodotorula glutinis; Saccharomyces cerevisiae* (See Yeast Mix); *Scopulariopsis brevicaulis; Spondylocladium sp.; Sporobolomyces salmonicolor; Stemphylium botryosum; Streptomyces griseus; Trichoderma viride; Typhula idahoensis; Verticillium albo-atrum*.

Smuts—Smut, Barley; Smut, Bermuda; Smut, Corn; Smut, Johnson; Smut, Oat; Smut, Sorghum; Smut, Wheat.

EXAMPLE 8

House Dust Extract

Repeating the extraction, filtration, ultrafiltration and lyophilization procedures of Example 1 but replacing the defatted Short Ragweed with house dust yielded the corresponding extracts.

EXAMPLE 9

Dust and Miscellaneous Extracts

Repeating the extraction, filtration, ultrafiltration and lyophilization procedures of Example 1 with the following dusts yields the corresponding elements: Acacia Gum; Alfalfa Hay; Algae, Chlorella spp.; Carragheen Gum; Coconut Fiber; Cotton Linters; Cottonseed; Dust, Barley; Dust, Corn; Dust, Grain Mill; Dust, Mattress; Dust, Oat; Dust, Pea; Dust, Rye; Dust, Soybean; Dust, upholstery; Dust, Wheat; Dust, Wood—Cedar/Juniper; Dust, Wood—Fir/Hemlock; Dust, Wood—Gum; Dust, Wood—Mahogany; Dust, Wood—Maple; Dust, Wood—Oak Mix; Dust, Wood—Pine Mix; Dust, Wood—Redwood; Dust, Wood—Spruce; Dust, Wood—Walnut; Fern Spores, sp.; Flax Fiber ; Flaxseed; Hemp; Jute; Kapok; karaya Gum; Lycopodium; Orris Root; Paper Mix; Pyrethrum; Silk; Sisal; Tragacanth Gum; Timothy Hay; Tobacco, Pipe; Tobacco, Cigarette; Tobacco, Cigar; Tobacco, Leaf.

EXAMPLE 10

FOOD EXTRACTS

Repeating the procedure of Example 1 but replacing the Short Ragweed with the following foods yields the corresponding extracts: Allspice; Almond; Apple Mix; Apricot Food; Arrowroot; Artichoke; Asparagus; Avocado; Banana; Barley, Whole (Grain); Bay Leaf; Bean, Kidney; Bean, Lima; Bean, Navy; Bean, Pinto-Frijole; Bean, String/Wax; Beef; Beet; Black-Eyed Pea; Blueberry; Brazil Nut; Buckwheat; Carrot; Cashew Nut; Celery; Cheese, Cheddar (American); Cheese, Parmesan; Cheese, Roquefort; Cheese, Swiss; Cherry Mix; Chewing Gum Base; chicken; Chicory; Chili Pepper; Chocolate/Cocoa; Cinnamon; Clam; Cloves; Cola; Coconut; Codfish Mix; Coffee; Corn, Whole (Grain); Crab; Cranberry; Cucumber; Curry Powder; Date; Dill; Egg White; Egg, Whole; Egg, Yolk; Eggplant; Endive; Garlic; Gelatine; Ginger; Grape/Raisin Mix; Grapefruit; Haddock; Halibut; Hazelnut (Filbert); Herring; Honey; Hops Food; Horseradish; Lamb; Lemon; Lentil; Lettuce Mix; Lime; Liver, Beef (Calves); Lobster; Mackerel; Malt; Mangoes; Maple, Syrup/Sugar; Melon, (see Muskmelon Mix); Milk, Cow's (Whole); Milk, Cow's (Albumin); Milk, Cow's (Casein); Milk, Cow's (Whey); Milk, (Evaporated); Milk, Goat's; Mint Mix (Peppermint/Spearmint); Mushroom; Mustard; Nutmeg; Oat, Whole (Grain); Okra; Olive Mix; Onion; Orange, Mandarin/Tangerine; Orange, Sweet; Oregano; Oyster Mix; Papaya; Paprika; Parsley; Parsnip; Pea; Peach Food; Peanut; Pear Food; Pecan Food; Pepper, Black/White; Pepper, Bell (Green/Red); Perch, Lake; Pineapple; Plum/Prune Mix; Poppy Seed; Pork; Potato, Sweet/Yam; Potato, White; Pumpkin; Rabbit Meat; Radish; Raspberry; Snapper; Rhubarb; Rice, Whole (Grain); Rice, Wild; Rye, Whole (Grain); Safflower Seed; Sage; Salmon; Scallops; Sesame Seed; Shrimp; Sole; Soybean, Whole (Grain); Spinach; Squash, Mix; Strawberry; Sugar (Beet); Sugar (Cane); Sunflower Seeds; Tapioca; Tea; Thyme; Tomato; Trout; Tuna Mix; Turkey; Turnip; Vanilla; Walnut Food, Black; Walnut Food, English; Watermelon; Wheat, Whole (Grain) Whitefish; Yeast, Bakers; Yeast, Brewers; Yeast Mix (Bakers/Brewers, Sacchoromyces cerevisiae).

EXAMPLE 11

Insect Extracts

Repeating the procedure of Example 1 but replacing the Short Ragweed pollen with the following insects yields the corresponding extracts: Ant, (Black and Red); Ants, Carpenter; Ants, Fire; Aphid; Bee, Bumble; Bee, Honey; Blackfly; Butterfly; Caddis Fly; Cricket; Cockroach Mix; Deer Fly; Flea Antigen; Fruit Flies; Gnat sp.; Hornet, Black & Yellow; Horse Fly; House Fly; Mayfly sp.; Mite (*D. farinae*); Mosquito Mix; Moth, Miller; Wasp; Yellow Jacket.

EXAMPLE 12

Insect Venom Extracts

Repeating the extraction, filtration, ultrafiltration, and lyophilization procedures set forth in Example 1 but replacing the defatted Short Ragweed pollen with the following insect venoms yields the corresponding extracts: Honey Bee Venom—*Apis mellifera*; Wasp Venom Protein—*Polistes sp.*; White-Faced Hornet Venom Protein—*Dolichovespula maculata*; Yellow Hornet Venom Protein—*Dolichovespula arenaria*; Yellow Jacket Venom Protein—*Vespula sp.*; Mixed Vespid Venom Protein.

EXAMPLE 13

Microtiter Plate Prep., Perennial Ryegrass Extract

Black polystyrene microtiter plates are cleaned with methanol and dried. Perennial ryegrass pollen extract prepared in Example 2 is reconstituted in phosphate buffered saline, pH 7.5 and diluted 1:200 with the phosphate buffered saline solution.

A 100 microliter quantity of the diluted extract is pipetted into a microtiter plate well, incubated for 2 hr at room temperature and removed, and the well is washed 3 times with a 5 to 10% aqueous solution of sucrose or sorbitol and dried to yield a microtiter plate well having Perennial Ryegrass pollen extract on its surface.

EXAMPLE 14

Microtiter Plate Preparation

Following the procedure of Example 13, black polystyrene microtiter plates are cleaned with methanol, and selected wells thereof are incubated with diluted, reconstituted extracts prepared in accordance with Examples 1–12 to yield microtiter plate wells having the corresponding extracts on the surface thereof.

EXAMPLE 15

Microtiter Plate, Covalent Bonding of Allergenic Extracts

Microtiter plate well inserts having a polylysine coating thereon are treated with solutions of reconstituted allergenic extracts prepared in accordance with Examples 1–12 and glutaraldehyde to yield microtiter plate well inserts having the corresponding extracts covalently bonded thereto.

EXAMPLE 16

Short Ragweed Pollen Extract-Frosted Glass Conjugates

The one hundred frosted glass tubes are immersed in 100 ml of 0.5% solution of $\gamma$-amino-propyltriethoxysilane in acetone. After incubation at room temperature for 10 hr, the tubes are removed and washed with methanol and then with water. The tubes having the amino-containing silane coupling agent bound thereto are immersed in 40 ml of normal saline solution. A solution of 50 mg of allergenic extract from Short Ragweed pollen obtained in accordance with Example 1 in 10 ml of physiological saline solution and a solution containing 0.2% N-ethyl-N'-dimethylaminopropylcarbodiimide in 10 ml of physiological saline solution are added thereto. After treatment under immersion at 37° C. for 2 hours, the tubes are washed in sequence with water, 1M propionic acid aqueous solution and water, until no protein was detected in the washings.

The bound protein content can be measured by the method described by S. Moore et al, in Methods in Enzymology 6.819(1963). 10 pieces of the protein-glass conjugate are immersed in a solution of 6N HCL; and the whole system is sealed under reduced pressure and heated at 110° for 30 hrs. The protein content is measured by ninhydrin coloration.

EXAMPLE 17

Allergenic Extract—Frosted Glass Conjugate

Repeating the procedure of Example 16 but replacing the Short Ragweed pollen extract with the extracts obtained in Examples 2–12 yields the corresponding, respective allergenic extract-glass conjugates.

EXAMPLE 18

Allergenic Extract-Frosted Glass Conjugates

Two hundred frosted glass beads are immersed in 100 ml of 0.5% solution of $\gamma$-aminopropyltriethoxysilane in toluene and boiled for 7 hrs. The beads are then filtered off and washed with methanol and then with water. To the 200 frosted glass beads to which the aminocontaining silane coupling agent has been bound, there is added 100 ml of 2% glutaraldehyde aqueous solution. After standing for 2 hours at 4°, the beads are washed with deionized water 4 to 6 times until they did not carry the odor of glutaraldehyde any more. The 200 frosted glass beads so treated are then immersed in 40 ml of normal saline solution. Thereto is added a solution of 50 mg Golden Rod pollen allergenic extract in 10 ml of physiological saline. After allowing the reaction to proceed at 30° for 2 hrs, the glass beads are thoroughly washed with water until no protein is detected in the washings.

Repeating the above procedure but replacing the Golden Rod pollen extract with extracts obtained according to Examples 1–12 yields the corresponding allergenic extract-glass conjugates.

The invention claimed is:

1. A process for increasing shelf life stability of an allergenic extract comprising
   (a) passing a solution of an unprecipitated allergenic extract through 100,000 and 1,000 dalton ultrafilters and retaining substantially all of the fraction having a molecular weight of from 1,000 to 100,000, and
   (b) substantially drying the retained fraction to yield an allergenic product which has an extended shelf life when dry and when reconstituted in an aqueous medium.

2. The process of claim 1 wherein the allergenic extract is derived from a member selected from the group consisting of pollens, epidermals, glandular elements, molds, smuts, insects, insect venoms and foods.

3. The process of claim 2 wherein the allergenic extract is derived from a pollen.

4. The process of claim 2 wherein the allergenic extract is derived from an epidermal or glandular element of an animal.

5. The process of claim 2 wherein the allergenic extract is derived from a mold.

6. The process of claim 2 wherein the allergenic extract is derived from a smut.

7. The process of claim 2 wherein the allergenic extract is derived from an insect.

8. The process of claim 7 wherein the allergenic extract is derived from an insect venom.

9. The process of claim 2 wherein the allergenic extract is derived from a food.

10. The process of claim 1 wherein the fraction is treated with from 0.5 to 2.5 Mrad of gamma radiation while at a moisture range of from 0.1 to 10 wt. % water.

11. The process of claim 1 wherein the solution of allergenic extract is contacted with an amylase bound to an insoluble support to reduce the starches therein to sugars before being passed through the 1000 dalton filter.

12. The process of claim 1 wherein the retained fraction is treated by affinity chromatography containing, on an insoluble support, at least one reagent conjugatable with a member selected from the group of proteolytic agents and carbohydrate reducing agents.

13. A substantially dried, stabilized allergenic extract consisting essentially of extracted allergens having molecular weights within the range of from 1,000 to 100,000, the extracted allergens being substantially free from extract components having molecular weights of less than 1,000 and greater than 100,000 the extract having an extended shelf life when dry and when reconstituted in an aqueous medium.

14. The stabilized allergenic extract of claim 13 wherein the extract is obtained from a member selected from the group consisting of pollens, epidermals, glandular elements, molds, smuts, insects, insect venoms and foods.

15. The allergenic extract of claim 14 obtained from a pollen.

16. The allergenic extract of claim 14 obtained from an epidermal or glandular element of an animal.

17. The allergenic extract of claim 14 obtained from a mold.

18. The allergenic extract of claim 14 obtained from a smut.

19. The allergenic extract of claim 14 obtained from an insect.

20. The allergenic extract of claim 14 obtained from an insect venom.

21. The allergenic extract of claim 14 obtained from a food.

22. The stabilized allergenic extract of claim 13 substantially free from active proteolytic enzyme.

23. The allergenic extract of claim 13 which has been treated with gamma radiation.

24. The allergenic extract of claim 23 which has been treated with from 0.5 to 2.5 Mrads of gamma radiation while at a moisture content of from 0.1 to 10 wt. %.

25. The allergenic extract of claim 13 substantially free from starches and sugars.

* * * * *